(12) United States Patent
Kumar et al.

(10) Patent No.: US 10,117,743 B2
(45) Date of Patent: Nov. 6, 2018

(54) HYBRID ORIENTATION PARAVALVULAR SEALING STENT

(71) Applicant: St. Jude Medical, Cardiology Division, Inc., St. Paul, MN (US)

(72) Inventors: Saravana B. Kumar, Otsego, MN (US); Sounthara Khouengboua, Chaska, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 39 days.

(21) Appl. No.: 14/901,287

(22) PCT Filed: Jun. 27, 2014

(86) PCT No.: PCT/US2014/044580
§ 371 (c)(1),
(2) Date: Dec. 28, 2015

(87) PCT Pub. No.: WO2015/002832
PCT Pub. Date: Jan. 8, 2015

(65) Prior Publication Data
US 2016/0158004 A1    Jun. 9, 2016

Related U.S. Application Data

(60) Provisional application No. 61/841,598, filed on Jul. 1, 2013.

(51) Int. Cl.
*A61F 2/24* (2006.01)
(52) U.S. Cl.
CPC .............. *A61F 2/2418* (2013.01); *A61F 2/24* (2013.01); *A61F 2/2412* (2013.01);
(Continued)

(58) Field of Classification Search
CPC .. A61F 2/24–2/2424; A61F 2250/0003; A61F 2250/0036; A61F 2250/0039; A61F 2250/0069–2250/007; A61F 2/2418
See application file for complete search history.

(56) References Cited

U.S. PATENT DOCUMENTS 6,425,916 B1    7/2002  Garrison et al.
2002/0138135 A1    9/2002  Duerig et al.
(Continued)

OTHER PUBLICATIONS

International Search Report and Written Opinion for Application No. PCT/US2014/044580 dated Dec. 12, 2014.

*Primary Examiner* — Yashita Sharma
*Assistant Examiner* — Rebecca Preston
(74) *Attorney, Agent, or Firm* — Lerner, Daivd, Littenberg, Krumholz & Mentlik, LLP

(57) ABSTRACT

A prosthetic heart valve (300) for replacing a native heart valve includes a collapsible and expandable stent (306) extending in a length direction between a proximal end (302) and a distal end (304), the stent (306) including a plurality of struts (320) defining a plurality of cells (330), the plurality of cells (330) forming an aortic section (310), an annulus section (314) and a subannular section (316) of the stent (306). A valve assembly is disposed within the annulus section (314) of the stent (306), the valve assembly including a plurality of leaflets. In an expanded condition of the stent, each of the plurality of cells of the subannular section (316) has a width greater than its length, and each of the plurality of cells of the annulus section (314) has a length greater than its width.

9 Claims, 7 Drawing Sheets

(52) U.S. Cl.
CPC ..... *A61F 2/2436* (2013.01); *A61F 2210/0014* (2013.01); *A61F 2210/0057* (2013.01); *A61F 2230/008* (2013.01); *A61F 2230/0078* (2013.01); *A61F 2250/001* (2013.01); *A61F 2250/0018* (2013.01); *A61F 2250/0029* (2013.01); *A61F 2250/0036* (2013.01); *A61F 2250/0039* (2013.01); *A61F 2250/0096* (2013.01)

(56) References Cited

U.S. PATENT DOCUMENTS

| | | | |
|---|---|---|---|
| 2007/0043435 A1* | 2/2007 | Seguin | A61F 2/2418 623/2.11 |
| 2008/0125859 A1* | 5/2008 | Salahieh | A61F 2/2415 623/2.11 |
| 2008/0208327 A1* | 8/2008 | Rowe | A61F 2/2418 623/2.11 |
| 2009/0171447 A1* | 7/2009 | Von Segesser | A61F 2/2418 623/1.24 |
| 2010/0004740 A1 | 1/2010 | Seguin et al. | |
| 2010/0049306 A1 | 2/2010 | House et al. | |
| 2010/0280597 A1 | 11/2010 | Hoerstrup et al. | |
| 2011/0238168 A1 | 9/2011 | Pellegrini et al. | |
| 2012/0123529 A1* | 5/2012 | Levi | A61F 2/2412 623/2.11 |
| 2012/0271398 A1* | 10/2012 | Essinger | A61F 2/2412 623/1.11 |
| 2012/0316642 A1* | 12/2012 | Yu | A61F 2/2412 623/2.13 |

* cited by examiner

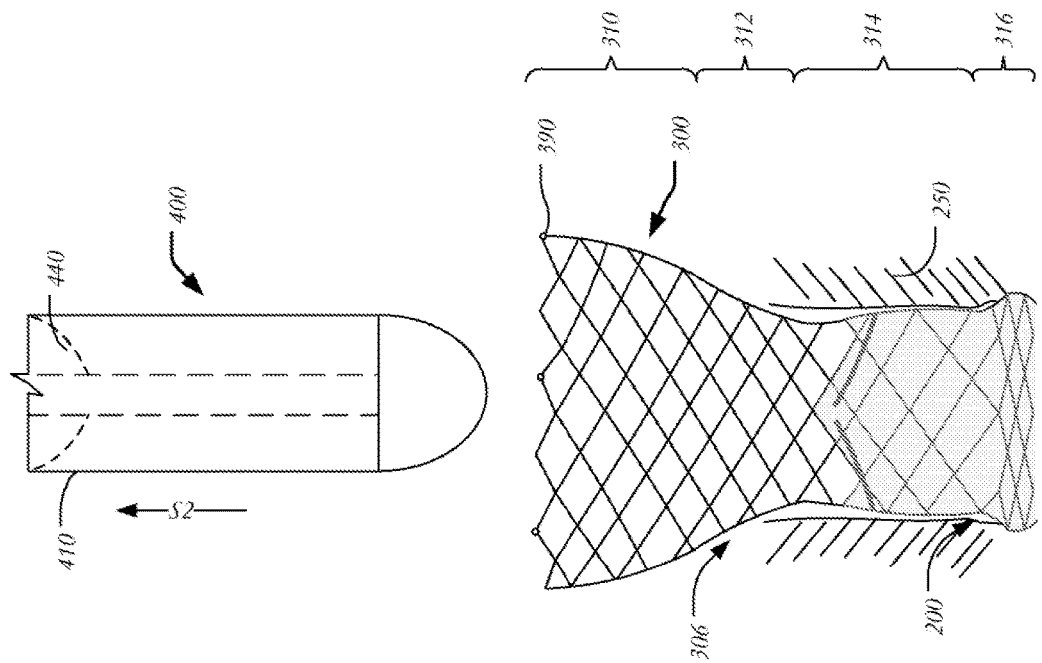
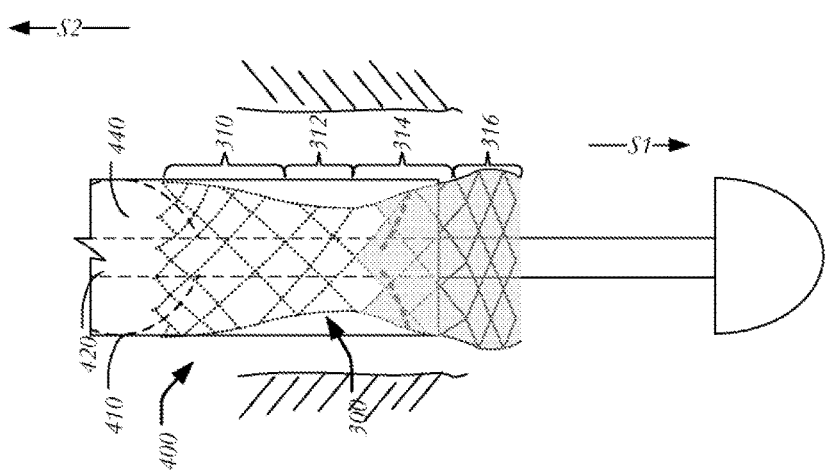
FIG. 4D
FIG. 4C

HYBRID ORIENTATION PARAVALVULAR SEALING STENT

CROSS-REFERENCE TO RELATED APPLICATION

This application is a national phase entry under 35 U.S.C. § 371 of International Application No. PCT/US2014/044580, filed Jun. 27, 2014, which claims priority to U.S. Provisional Patent Application No. 61/841,598, filed Jul. 1, 2013, the disclosures of which are incorporated herein by reference.

BACKGROUND OF THE INVENTION

The present disclosure relates in general to heart valve replacement and, in particular, to collapsible prosthetic heart valves. More particularly, the present disclosure relates to devices and methods for positioning and sealing collapsible prosthetic heart valves within a native valve annulus.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a snore invasive procedure such as full open-chest, open-heart surgery.

Collapsible prosthetic heart valves typically take the form of a valve structure mounted on a stent. There are two common types of stents on which the valve structures are ordinarily mounted: a self-expanding stent or a balloon-expandable stent. To place such valves into a delivery apparatus and ultimately into a patient, the valve must first be; collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, and then expanding a balloon positioned within the valve stent. For self-expanding valves, on the other hand, the stent automatically expands as the sheath covering the valve is withdrawn.

SUMMARY OF THE INVENTION

In some embodiments, a method implanting a prosthetic heart valve includes delivering the prosthetic heart valve in a collapsed condition to the native valve annulus, the heart valve including: (i) a collapsible and expandable stent extending in a length direction between a proximal end and a distal end and including a plurality of struts defining a plurality of cells, the plurality of cells forming an aortic section, an annulus section and a subannular section of the stent, each of the cells having a length in the length direction and a width in a circumferential direction of the stent, and (ii) a valve assembly disposed within the annulus section of the stent, the valve assembly including a plurality of leaflets; and transitioning the stent from the collapsed condition to an expanded condition, whereby the plurality of cells of the subannular section foreshorten in the length direction by a first relative amount and the plurality of cells of the annulus section foreshorten in the length direction by a second relative amount less than the first relative amount.

In some embodiments, a prosthetic heart valve for replacing a native valve includes a collapsible and expandable stent extending in a length direction between a proximal end and a distal end, the stent including a plurality of struts defining a plurality of cells, the plurality of cells forming an aortic section, an annulus section and a subannular section of the stent, and a valve assembly disposed within the annulus section of the stent, the valve assembly including a plurality of leaflets. The subannular section in an expanded condition of the stent may have a larger diameter than the annulus section in the expanded condition of the stent.

In some embodiments, a prosthetic heart valve for replacing a native valve includes a collapsible and expandable stent having a proximal end, a distal end, and a plurality of struts defining a plurality of cells, the plurality of cells forcing an aortic section, an annulus section and a subannular section of the stent, and a valve assembly disposed within the annulus section of the stent, the valve assembly including a plurality of leaflets. The struts of the annulus section may have a first average thickness and the struts of the subannular section have a second average thickness different from the first average thickness.

In some embodiments, a prosthetic heart valve for replacing a native valve includes a collapsible and expandable stent extending in a length direction between a proximal end and a distal end, the stent including a plurality of struts defining a plurality of cells, the plurality of cells forcing an aortic section, an annulus section and a subannular section of the stent, each of the cells having a length in the length direction and a width in a circumferential direction of the stent and a valve assembly disposed within the annulus section of the stent, the valve assembly including a plurality of leaflets. In an expanded condition of the stent, each of the plurality of cells of the subannular section has a width greater than its length, and each of the plurality of cells of the annulus section had a length greater than its width.

BRIEF DESCRIPTION OF THE DRAWINGS

Various embodiments of the present invention will now be described with reference to the appended drawings. It is to be appreciated that these drawings depict only some embodiments of the invention and are therefore not to be considered limiting of its scope.

FIGS. 4A-D are highly schematic side views of one method of delivering and deploying the heart valve of FIG. 3A within the native valve annulus.

DETAILED DESCRIPTION

Despite the various improvements that have been made to the collapsible prosthetic heart valve delivery process, conventional devices suffer from some shortcomings. For example, with conventional self expanding valves, clinical success of the valve is dependent on accurate deployment and anchoring. Inaccurate deployment and anchoring of the valve increases risks, such as those associated with valve migration, which may cause severe complications due to the obstruction of the left ventricular outflow tract. Inaccurate deployment and anchoring may also result in the leakage of blood between the implanted heart valve and the native valve annulus, commonly referred to as perivalvular leakage (also known as "paravalvular leakage"). In aortic valves, this leakage enables blood to flow from the aorta back into the left ventricle, reducing cardiac efficiency and putting a greater strain on the heart muscle. Additionally, calcification of the aortic valve may affect performance and the interaction between the implanted valve and the calcified tissue is believed to be relevant to leakage, as will be outlined below.

Moreover, anatomical variations from one patient to another may cause a fully deployed heart valve to function improperly, requiring removal of the valve from the patient. Removing a fully deployed heart valve increases the length of the procedure as well as the risk of infection and/or damage to heart tissue. Thus, methods and devices are desirable that would reduce the need to remove a prosthetic heart valve from a patient. Methods and devices are also desirable that would reduce the likelihood of perivalvular leakage due to gaps between the implanted heart valve and patient tissue.

There is a need for further improvements to the devices, systems, and methods for transcatheter delivery and positioning of collapsible prosthetic heart valves. Specifically, there is a need for further improvements to the devices, systems, and methods for accurately implanting a prosthetic heart valve. Among other advantages, the present disclosure may address one or more of these needs.

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient.

Figure 1:
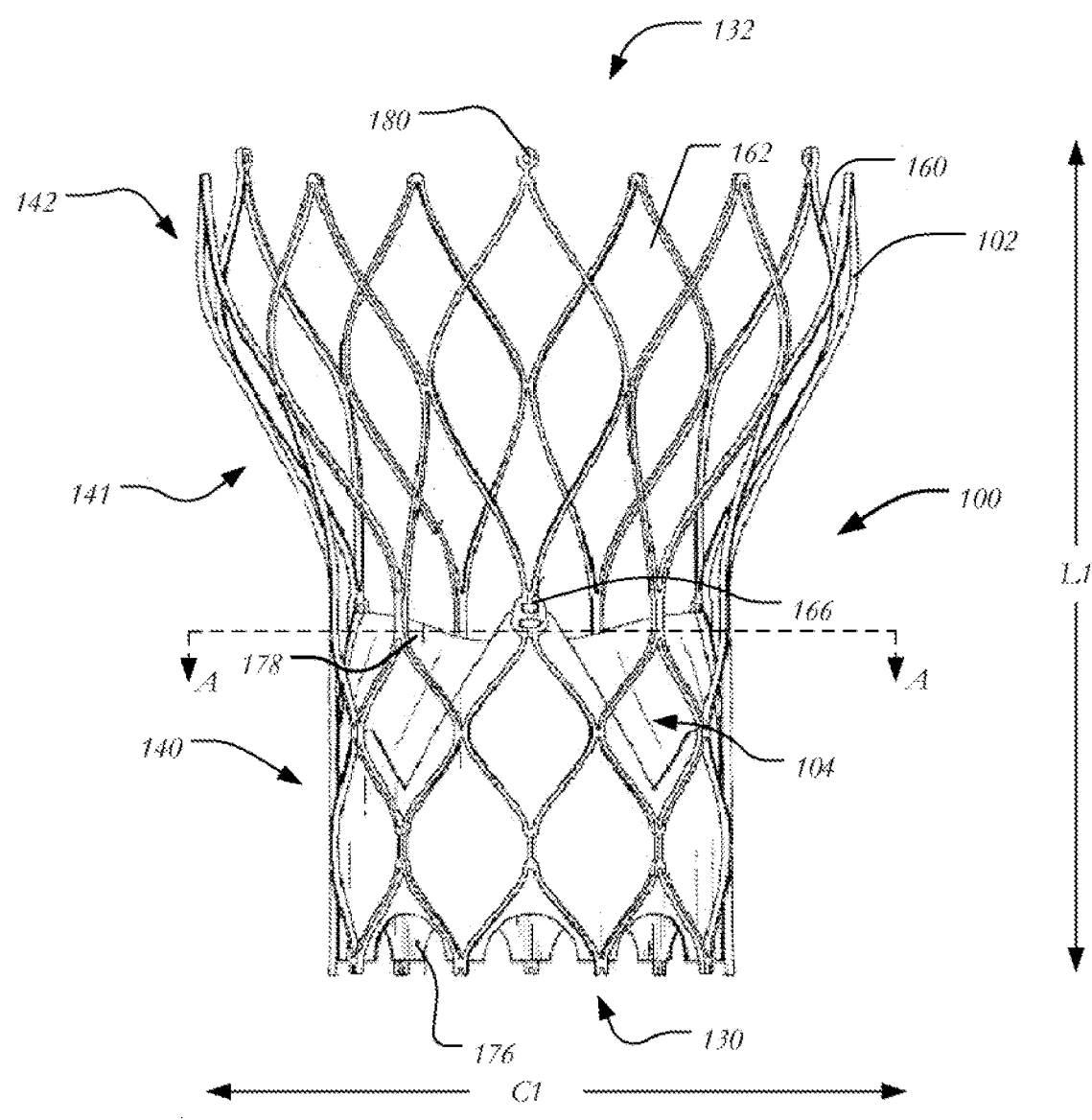
FIG. 1 is a side elevational view of a conventional prosthetic heart valve.

The features of the present disclosure may be used in connection with collapsible prosthetic heart valves. FIG. 1 shows one such collapsible stent-supported prosthetic heart valve 100 including a stent 102 and a valve assembly 104 as is known in the art. The prosthetic heart valve 100 is designed to replace a native tricuspid valve of a patient, such as a native aortic valve. It should be noted that while the inventions herein are described predominately in connection with their use with a prosthetic aortic valve and a stent having a shape as illustrated in FIG. 1, the valve could be a bicuspid valve, such as the mitral valve, and the stent could have different shapes, such as a flared or conical annulus section, a less-bulbous aortic section, and the like, and a differently shaped transition section.

The expandable stent 102 of prosthetic heart valve 100 may be forced from biocompatible materials that are capable of self-expansion, such as, for example, shape memory alloys, such as the nickel-titanium alloy known as "Nitinol" or other suitable metals or polymers. Stent 102 extends in a length direction L1 from proximal or annulus end 130 to distal or aortic end 32, and includes annulus section 140 adjacent proximal end 130, transition section 141 and aortic section 142 adjacent distal end 132. Annulus section 140 has a relatively small cross-section in the expanded condition, while aortic section 142 has a relatively large cross-section in the expanded condition. Preferably, annulus section 140 is in the form of a cylinder having a substantially constant diameter along its length. Transition section 141 may taper outwardly from annulus section 140 to aortic section 142. Each of the sections of stent 102 includes a plurality of struts 160 forming cells 162 connected to one another in one or more annular rows around the stent. For example, as shown in FIG. 1, annulus section 140 may have two annular rows of complete cells 162 and aortic section 142 and transition section 141 may each have one or more annular rows or partial cells 162. Cells 162 in aortic section 142 may be larger than cells 162 in annulus section 140. The larger cells in aortic section 142 better enable prosthetic valve 100 to be positioned in the native valve annulus without the stent structure interfering with blood flow to the coronary arteries. Each of cells 162 have a length in length direction L1 and a width in circumferential direction C1 of the stent Stent 102 may include one or more retaining elements 168 at distal end 132 thereof, retaining elements 168 being sized and shaped to cooperate with female retaining structures (not shown) provided on a deployment device. The engagement of retaining elements 168 with the female retaining structures on the deployment device helps maintain prosthetic heart valve 100 in assembled relationship with the deployment device, minimizes longitudinal movement of the prosthetic heart valve relative to the deployment device during unsheathing or re sheathing procedures, and helps prevent rotation of the prosthetic heart valve relative to the deployment device as the deployment device is advanced to the target location and the heart valve deployed.

Valve assembly 104 of prosthetic heart valve 100 preferably is positioned in annulus section 140 of stent 102 and secured to the stent. Valve assembly 104 includes cuff 176 and a plurality of leaflets 178 which collectively function as a one-way valve by coapting with one another. As a prosthetic aortic valve, valve 100 has three leaflets 178. However, it will be appreciated that other prosthetic heart valves with which the sealing portions of the present disclosure may be used may have a greater or lesser number of leaflets 178.

Although cuff 176 is shown in FIG. 1 as being disposed on the luminal or inner surface of annulus section 140, it is contemplated that cuff 176 may be disposed on the abluminal or outer surface of annulus section 140 or may cover all or part of either or both of the luminal and abluminal surfaces. Both cuff 176 and leaflets 178 may be wholly or partly formed of any suitable biological material or polymer such as, for example, polytetrafluoroethylene (PTFE).

Leaflets 178 may be attached along their belly portions to cells 162 of stent 102, with the commissure between adjacent leaflets 178 attached to a commissure feature 180. As can be seen in FIG. 1, each commissure feature 180 may lie at the intersection of four cells 162, two of the cells being adjacent one another in the same annular row, and the other two cells being in different annular rows and lying in end-to-end relationship. Preferably, commissure features 180 are positioned entirely within annulus section 140 or at the juncture of annulus section 140 and transition section 141. Commissure features 180 may include one or more eyelets which facilitate the suturing of the leaflet commissure to stent 102.

Prosthetic heart valve 100 may be used to replace a native aortic valve, a surgical heart valve or a heart valve that has undergone a surgical procedure. Prosthetic heart valve 100 may be delivered to the desired site (e.g., near the native aortic annulus) using any suitable delivery device. During delivery, prosthetic heart valve 100 is disposed inside the delivery device in the collapsed condition. The delivery device may be introduced into a patient using a transfemoral, transapical, transseptal or any other percutaneous approach. Once the delivery device has reached the target site, the user may deploy prosthetic heart valve 100. Upon deployment, prosthetic heart valve 100 expands so that annulus section 140 is in secure engagement within the native aortic annulus. When prosthetic heart valve 100 is properly positioned inside the heart, it works as a one-way valve, allowing blood to flow from the left ventricle of the heart to the aorta, and preventing blood from flawing in the opposite direction.

Problems may be encountered when implanting prosthetic heart valve 100. For example, in certain procedures, collapsible valves may be implanted in a native valve annulus without first resecting the native valve leaflets. The collapsible valves may have critical clinical issues because of the nature of the stenotic leaflets that are left in place. Additionally, patients with uneven calcification, bi-cuspid aortic valve disease, and/or valve insufficiency cannot be treated well, if at all, with the current collapsible valve designs.

The reliance on unevenly calcified leaflets for proper valve placement and seating could lead to several problems, such as perivalvular leakage (PV leak), which can have severe adverse clinical outcomes. To reduce these adverse events, the optimal valve would anchor adequately and seal, without the need for excessive radial force that could harm nearby anatomy and physiology.

Figure 2:
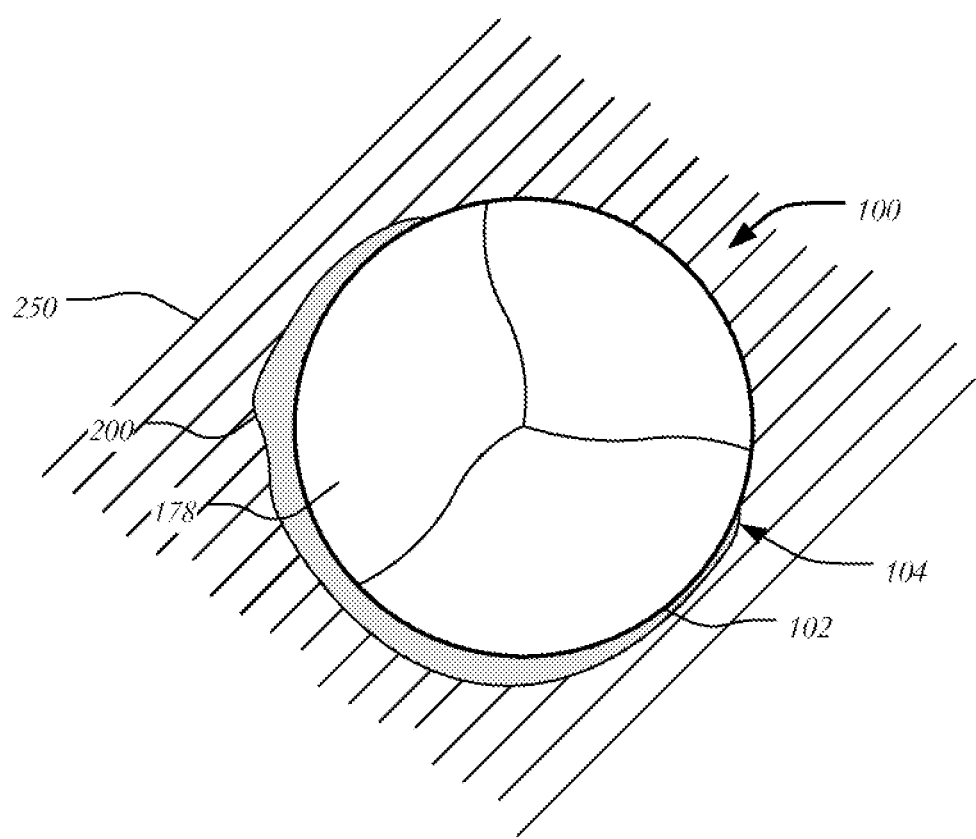
FIG. 2 is a highly schematic cross-sectional view taken along line A-A of FIG. 1 and showing the prosthetic heart valve disposed within a native valve annulus.

FIG. 2 is a highly schematic cross-sectional illustration of prosthetic heart valve 100 disposed within native valve annulus 250. As seen in the figure, valve assembly 104 has a substantially circular cross-section which is disposed within the non-circular native valve annulus 250. At certain locations around the perimeter of heart valve 100, gaps 200 form between heart valve 100 and native valve annulus 250. Blood flowing through these gaps and past valve assembly 104 of prosthetic heart valve 100 can cause regurgitation and other inefficiencies which reduce cardiac performance. Such improper fitment may be due to suboptical native valve annulus geometry due, for example, to calcification of native valve annulus 250 or to unresected native leaflets.

Figure 3A:
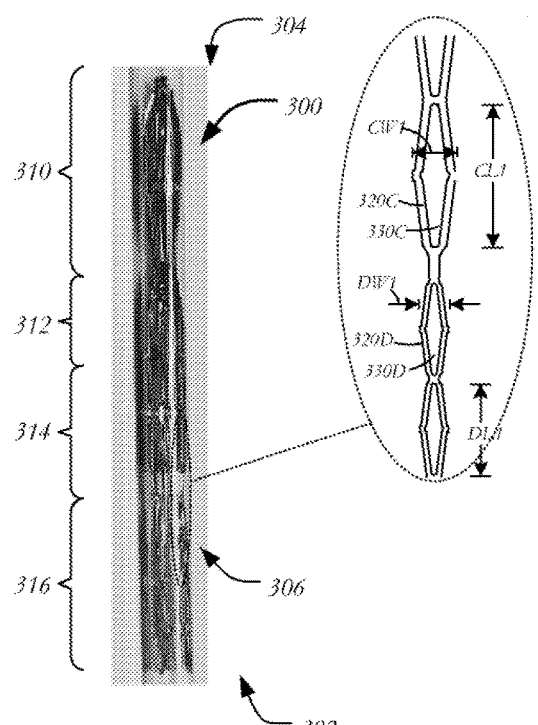
FIG. 3A is a highly schematic side elevational view of one embodiment of a prosthetic heart valve having an enlarged subannular section intended to fill irregularities between the heart valve and the native valve annulus.
Figure 3B:
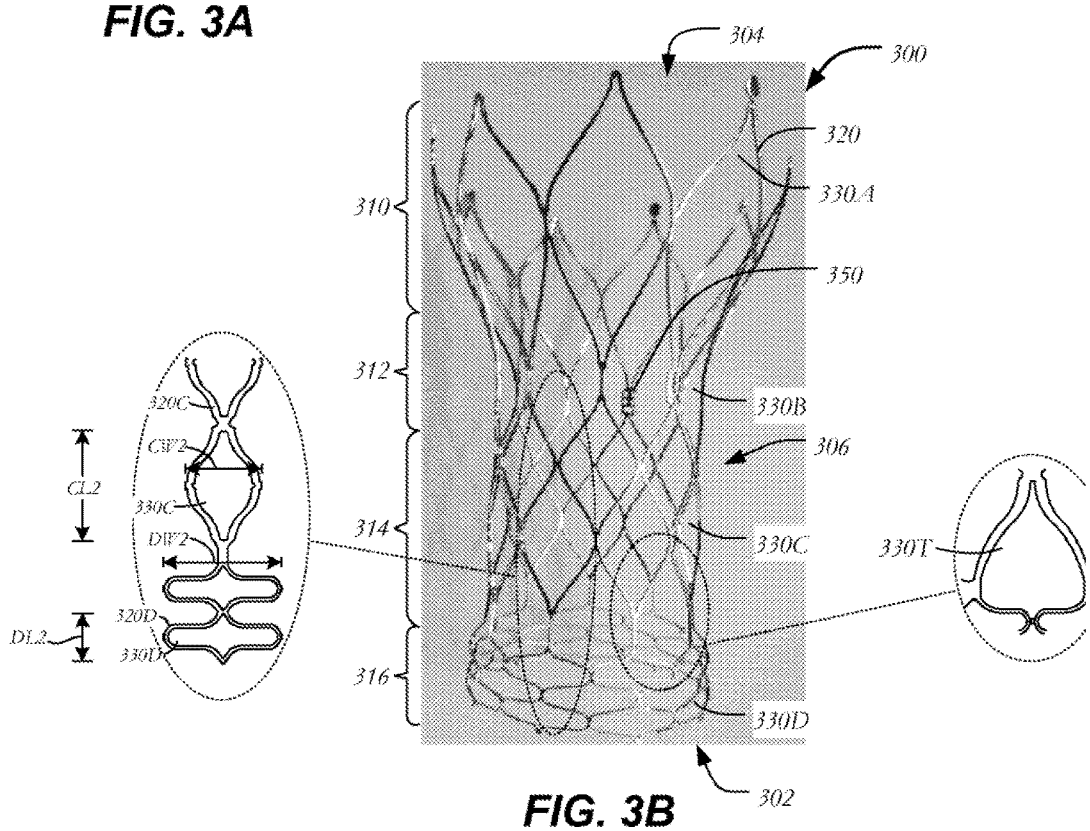
FIG. 3B is a perspective view of the prosthetic heart valve of FIG. 3A.

FIGS. 3A and 3B illustrate one embodiment of prosthetic heart valve 300 intended to fill the irregularities between the implanted heart valve and native valve annulus 250 shown in FIG. 2. FIG. 3A illustrates heart valve 300 in the collapsed condition for delivery and FIG. 3B illustrates heart valve 300 in the expanded condition after implantation. Heart valve 300 extends in a length direction between proximal end 302 and distal end 304, and may generally include stent 306 and a valve assembly having a plurality of leaflets and a cuff as described, above (not shown for the sake of clarity). Heart valve 300 may be formed of any of the materials described above with reference to FIG. 1 and may be preset (e.g., heat set) to the expanded condition and crimped into the collapsed, condition for delivery.

From distal end 304 to proximal end 302, stent 306 may include in series aortic section 310, transition section 312, annulus section 314 and subannular section 316. Aortic section 310, transition section 312 and annulus section 314 may be configured similarly to the embodiment described with reference to FIG. 1. Specifically, annulus section 314, which supports the valve assembly, has a relatively small cross-section in the expanded condition, while aortic section 310 has a relatively large cross-section in the expanded condition. Preferably, annulus section 314 is in the form of a cylinder having a substantially constant diameter along its length. Transition section 312 may taper outwardly from annulus section 314 to aortic section 310. In contrast to the embodiment described with respect to FIG. 1, subannular section 316 may be coupled to annulus section 314 and configured to minimize perivalvular leakage due to its shape and function.

Each or the sections of stent 306 includes a plurality of struts 320 forming cells 330 connected to one another in one or more annular rows around stent 306. Generally, cells 330A of aortic section 310 may be larger than cells 330C of annulus section 314, and cells 330B of transition section 312 may be smaller than cells 330A and larger than cells 330C. The larger cells 330 A in aortic section 310 better enable prosthetic valve 300 to be positioned in the native valve annulus without the stent structure interfering with blood flow to the coronary arteries. Thus, cells 330 may differ in size depending on their position on stent 306 and their function. Moreover, differences between cells 330C of annulus section 314 and cells of 330D of subannular section 316 may contribute to minimizing perivalvular leakage.

When prosthetic heart valve 300 transitions between the collapsed condition for delivery (FIG. 3A) and the expanded condition for implantation (FIG. 3B), each of cells 330 of stent 306 foreshortens by a predetermined amount. Specifically, cells 330C of annulus section 314 foreshorten from a length CL1 in the collapsed condition to a length CL2 in the expanded condition. The length of cells 330 refers to the dimension of the cells in the length direction of heart valve 300. In some examples, CL1, the length of cells 330C in the collapsed condition, is between about 12 mm and about 24 mm and CL2, the length of cells 330C in the expanded condition, is between about 9 mm and about 20 mm. Thus, the length of cells 330C of annulus section 314 may foreshorten by between about 10% and about 18% from the collapsed condition to the expanded condition. Likewise, cells 330D of subannular section 316 foreshorten from a length DL1 in the collapsed. condition to a length DL2 in the expanded condition. In some examples, DL1 is between about 10 mm and about 24 mm and DL2 is between about 5 mm and about 1.2 mm. The length of cells 330D of subannular section 316 may foreshorten by between about 50% and about 100% from the collapsed, condition to the expanded condition. Thus, cells 330D of subannular section 316 may foreshorten to a greater degree than cells 330C of annulus section 314. In some examples, cells 330D of subannular section 316 may foreshorten between about three and about five times more than cells 330C of annulus section 314. Due to the foreshortening of cells 330, annulus section 314 collectively foreshortens by between about 10% and about 18%, while subannular section 316 collectively foreshortens by between about 50% and about 100%.

The length of each cell 330 is inversely proportional to the width of the cell in the circumferential direction of heart valve 300. Thus, as each cell 330 foreshortens from the collapsed condition to the expanded condition, the width of the cell 330 increases. In some examples, CW1, the width of cells 330C in the collapsed condition, is between about 1 mm and about 4 mm and CW2, the width of cells 330C in the expanded condition, is between about 7 mm and about 12 mm. Thus, the width of cells 330C of annulus section 314 may increase by between about 300% and about 1000% from the collapsed condition to the expanded condition. Likewise, cells 330D of subannular section 316 increase in width from a width DW1 in the collapsed condition to a width DW2 in the expanded condition. In some examples, DW1 is between about 1 mm and about 4 mm and DW2 is between about 9 mm and about 16 mm. Thus, cells 330D of subannular section 316 may increase in width by between about 500% and about 1500% from the collapsed condition to the expanded condition. Cells 330D of subannular section 316 may increase in width to a greater degree than cells 330C of annulus section 314. In some examples, cells 330D of subannular section 316 may increase in width by between about 20% and about 300% more than cells 330C of annulus section 314. Moreover, due to the foreshortening of cells 330 and the increase in width of each cell, annulus section 314 may effectively increase in diameter by between about 300% and about 500%, while subannular section 316 effectively increases in diameter by between about 400% and about 650%. Essentially, subannular section 316 functions as a Chinese finger trap (e.g., lengthening and narrowing in the collapsed condition and foreshortening and widening in the expanded condition). In at least some examples, subannular section 316 is between about 2 mm and about 6 mm larger in diameter than annulus section 314 in the expanded condition.

In the expanded condition, cells 330C in annulus section 314 are generally diamond-shaped and have a length CL2 that is greater than their width CW2. Conversely, cells 330D in subannular section 316 are generally oval-shaped with upper and lower peaks and a length DL2 that is less than their width DW2. Thus, the major axis of oval-shaped cells 330D are opositely oriented to the longest diagonal of diamond-shaped cells 330C in the fully expanded condition of heart valve 300. Disposed between rows of cells 330C of annulus section 314 and cells 330D of subannular section 316 is a row of transition cells 330T. Transition cells 330T may be generally mitre-shaped and have shared characteristics with both cells 330C and cells 330D (e.g., the tops of transition cells 330T resemble cells 330C while the bottoms of transition cells 330T resemble cells 330D). Transitions cells 330T may provide separation of valve functionality at annulus section 314 from perivalvular sealing at subannular section 316. Radial strength of transition cells 330T may be tailored to provide structural integrity, anchoring forces and deformation resistance due to annular motion.

As previously noted, annulus section 314 supports the valve assembly while subannular section 316 is configured to minimize perivalvular leakage. Because of the different functions of these sections, the average thickness of struts 320C in annulus section 314 may differ from the average thickness of struts 320D in subannular section 316. Specifically, the average thickness of struts 320C of annulus section 314 may be between about 0.01 inches (0.254 mm) and about 0.02 inches (0.508 mm) to provide strength to the stent structure and support for the valve assembly. Because struts 320D of subannular section 316 are intended to be conformable to the patient's anatomy to minimize perivalvular leakage, and because subannular section 316 does not primarily serve a supportive function, the average thickness of struts 320 may be between about ⅓ to ½ of the average thickness of struts 320C (e.g., between about 0.0033 inches (0.08382 mm) and about 0.01 inches (0.254 mm)). Due to this decreased thickness of struts 330D, subannular section 316 is radially conformable and may more easily change shape to adapt to the surrounding anatomy.

Figure 3C:
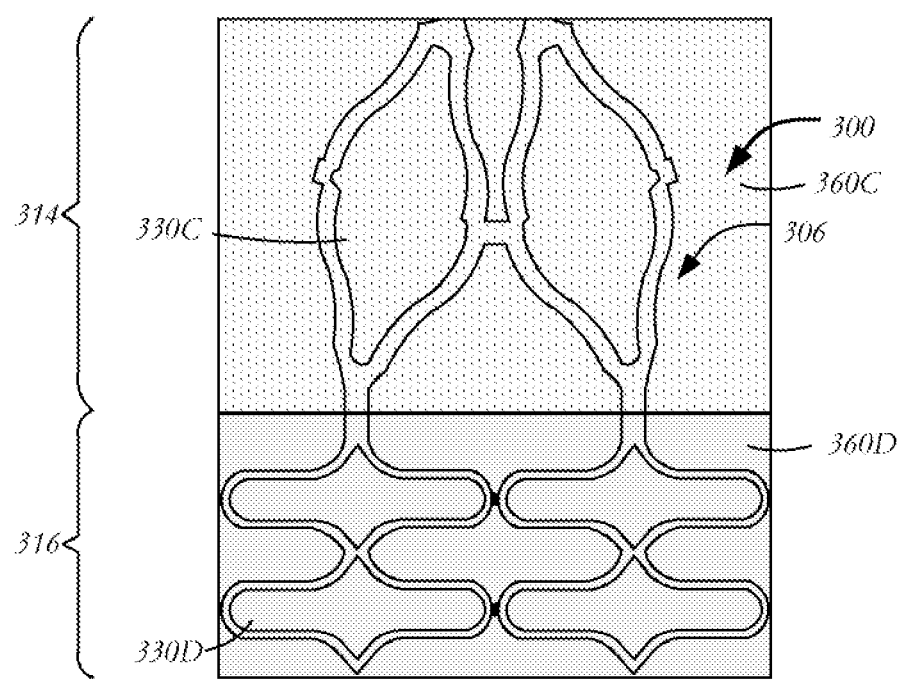
FIG. 3C is a highly schematic enlarged view of a portion of the annulus and subannular sections of a stent and a cuff portion corresponding to each section.

Though the valve assembly is not shown in FIGS. 3A and 3B, it is to be understood that a valve assembly including a cuff and a plurality of leaflets may be coupled to annulus section 314. Specifically, stent 306 includes commissure features 350 for attaching the leaflets thereto. Moreover, the cuff may be coupled to the luminal or abluminal surface of stent 306. In some examples, the cuff may extend beyond annulus section 314 to cover subannular section 316 as well as annulus section 314. Alternatively, as shown in FIG. 3C, two cuffs may be utilized to complete prosthetic heart valve 300. A first cuff 360C may be disposed about and coupled to annulus section 314 of stent 306 through conventional means such as sutures, glue or other adhesive. An independent second cuff 360D may be disposed about and coupled to subannular section 316 in a similar fashion. Second cuff 360D may be formed of the same material as cuff 360C, including natural materials such as, for example, bovine or porcine pericardium, or synthetic materials such as, for example, ultra-high-molecular-weight polyethylene (UHMWPE), or combinations thereof. Alternatively, second cuff 360D and first cuff 360C may be formed of different materials.

A method of delivering and implanting heart valve 300 will now be described with reference to FIGS. 4A-D. A delivery system 400 may be used to deliver and deploy heart valve 300 in native valve annulus 250, and may generally include sheath 410, core 420, atraumatic tip 430 and hub 440 coupled to core 420. Sheath 410 may be slidable relative to core 420. Prosthetic heart valve 300 may be disposed within sheath 410 with stent 306 in a collapsed condition about core 420 (FIG. 4A) and retaining elements 390 of heart valve 300 coupled to hub 440. By collapsing all sections of stent 306, heart valve 300 may be delivered to native valve annulus 250 using delivery system 400 without increasing the radius of sheath 410. A large delivery system may be incapable of being passed through the patient's vasculature, whereas a delivery system for a heart valve with a smaller crimp profile may be easier to navigate through a patient's body and may also reduce the operation time. In the example shown in FIGS. 4A-D, delivery system 400 is delivered from the aorta toward the left ventricle as indicated by arrow S1, although other approaches are equally possible. If heart valve 300 or delivery system 400 includes echogenic materials, such materials may be used to guide delivery system 400 to the appropriate position using the assistance of three-dimensional echocardiography to visualize heart valve 300 within the patient. Alternative visualization techniques known in the art are also contemplated herein.

Figure 4A:
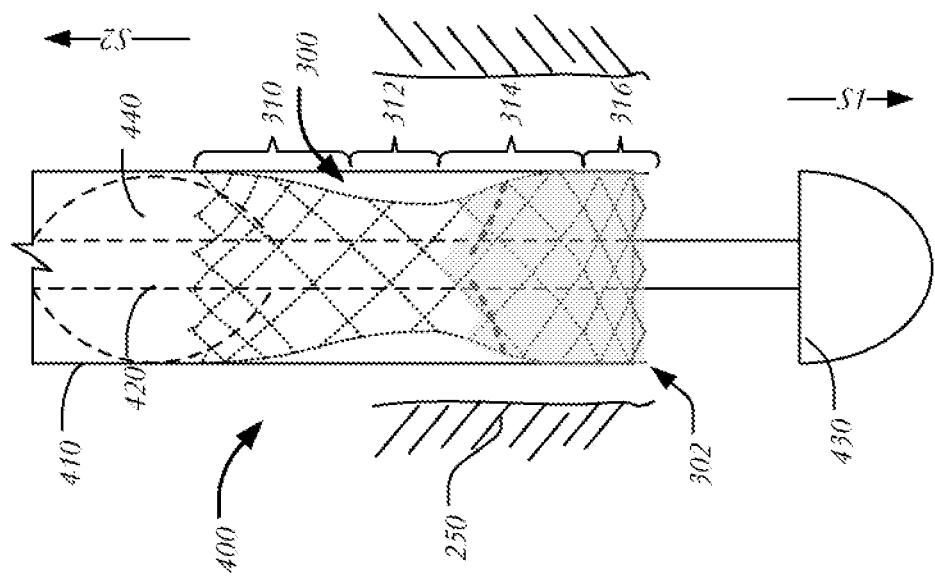
Figure 4B:
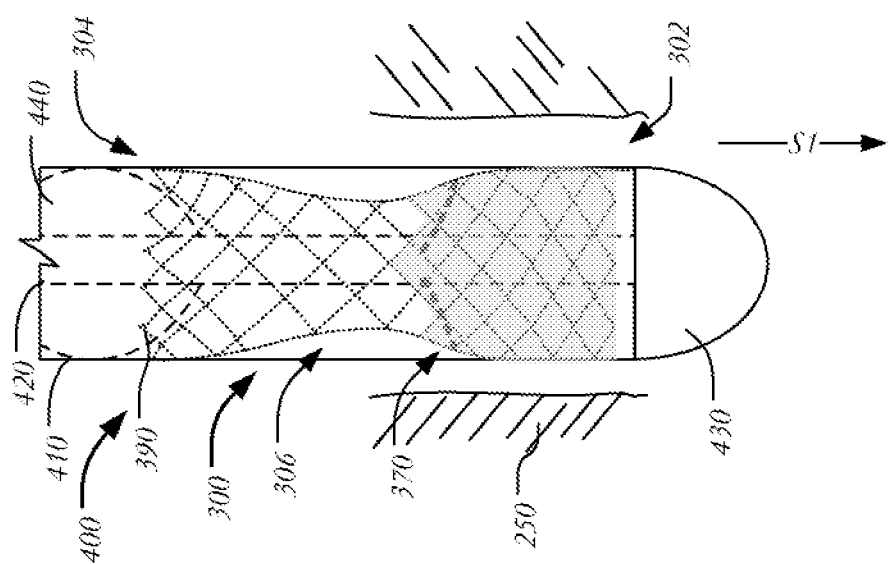

When delivery system 400 has reached the proper location (e.g. atraumatic tip 430 is just past native valve annulus 250), atraumatic tip 430 may be advanced slightly in the direction of arrow S1 toward the left ventricle by pushing core 420 toward atraumatic tip 430 while holding sheath 410 in place which serves to decouple atraumatic tip 430 from sheath 410 (FIG. 4B). Sheath 410 may then be retracted in the direction of arrow S2 toward the aorta. As seen in FIG. 4B, with sheath 410 slightly retracted, heart valve 300 begins to emerge from the sheath, beginning with subannular section 316 at proximal end 302. As sheath 410 is further retracted, in the direction of arrow S2, more of subannular section 316 of stent 306 is exposed (FIG. 4C). At this juncture, only subannular section 316 is exposed and the remaining portions of stent 306 are still disposed within sheath 410. While heart valve 300 is partially deployed (e.g., only subannular section 316 is outside sheath 410, and heart valve 300 is not fully detached from delivery system 400), if it appears that heart valve 300 needs to be recaptured and redeployed due to, for example, improper positioning or orientation, sheath 410 may be slid over core 420 in the direction of arrow S1 to recapture heart valve 300 within sheath 410. During recapture, sheath 410 may push against the edges of stent 306, stent 306 collapsing inside sheath 410 in the process. This procedure may be repeated until heart valve 300 is properly positioned.

After ascertaining proper positioning, sheath 410 may be withdrawn to expose annulus section 314, followed by transition section 312 and finally aortic section 310, thereby releasing all of stent 306 from sheath 410 (FIG. 4D). As noted above, heart valve 300 may be recaptured and redeployed. This procedure may be performed at any point until decoupling of retaining elements 390 of heart valve 300 from hub 440. Upon satisfactory positioning, retaining elements 390 of heart valve 300 may be decoupled from hub 440 and delivery system 400 may then be retracted through heart valve 300 in the direction of arrow S2 and removed from the patient.

As seen in FIG. 4D, heart valve 300 expands to fill native valve annulus 250. Specifically, subannular section 316 radially expands as cells 330D foreshorten as described above, occluding gaps 200 between heart valve 300 and native valve annulus 250, and thereby reducing or eliminating the amount of blood that passes around heart valve 300 through gaps 200. In some examples, subannular section 316 may expand below the leaflets of native valve annulus 250. Alternatively, subannular section 316 may expand within gaps in the native valve annulus.

Figure 5:
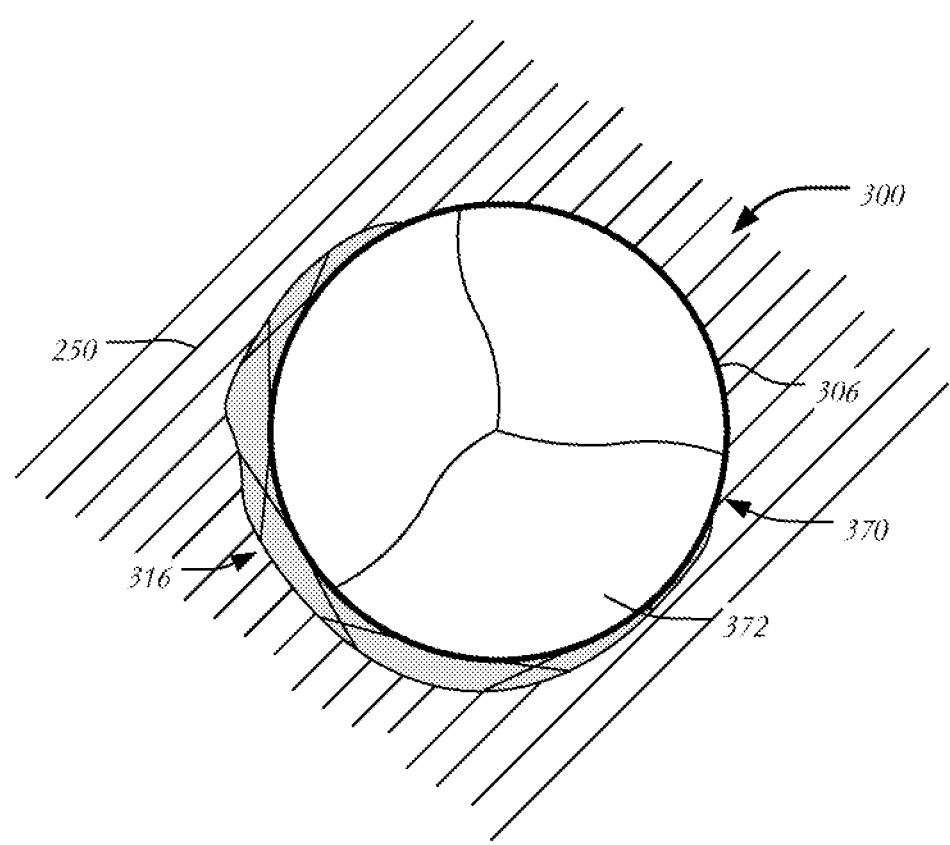
FIG. 5 is a highly schematic cross-sectional view showing a prosthetic heart valve having an enlarged subannular region disposed within a native valve annulus.

FIG. 5 is a highly schematic cross-sectional view showing heart valve 300 having stent 306 and valve assembly 370, including a cuff (not shown) and leaflets 372, the stent having a number of sections including subannular section 316. Heart valve 300 has been disposed within native valve annulus 250. As seen in FIG. 5, subannular section 316 has radially expanded fully to fill gaps 200 shown in FIG. 2, and may be capable of promoting tissue growth between heart valve 300 and native valve annulus 250. For example, portions of subannular section 316 may be innately capable of promoting tissue growth and/or may be treated with a biological or chemical agent to promote tissue growth, further enabling subannular section 316, when expanded, to seal the heart valve within the native valve annulus. Alternatively, the expanded subannular section 316 may be sufficiently dense to adequately seal around heart valve 300 without the need for major tissue growth. When subannular section 316 is functioning properly, heart valve 300 will be adequately sealed within native valve annulus 250 so that blood flows through leaflets 372 of valve assembly 370, and so that blood flow through any gaps formed between heart valve 300 and native valve annulus 250 is limited or reduced.

While the inventions herein have been described for use in connection with heart valve stents having a particular shape, the stent could have different shapes, such as a flared or conical annulus section, a less-bulbous aortic section, and the like, as well as a differently shaped transition section.

Moreover, although the inventions herein have been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present inventions as defined by the appended claims.

In some embodiments, a prosthetic heart valve for replacing a native valve includes a collapsible and expandable stent extending in a length direction between a proximal end and a distal end, the stent including a plurality of struts defining a plurality of cells, the plurality of cells forming an aortic section, an annulus section and a subannular section of the stent, each of the cells having a length in the length direction and a width in a circumferential direction of the stent and a valve assembly disposed within the annulus section of the stent, the valve assembly including a plurality of leaflets. In an expanded condition of the stent, each of the plurality of cells of the subannular section has a width greater than its length, and each of the plurality of cells of the annulus section had a length greater than its width.

In some examples, the plurality of cells may include a plurality of mitre-shaped transition cells disposed between the annulus section and the subannular section. The plurality of cells of the subannular section in the expanded condition may be generally oval-shaped with upper and lower peaks. The struts of the subannular section may have an average thickness less than an average thickness of the struts of the annulus section. The struts of the subannular section may have an average thickness between about ⅓ to about ½ of an average thickness of struts of the annulus section. The subannular section may be configured and arranged to be disposed below leaflets of the native valve when the prosthetic valve replaces the native valve.

In some embodiments, a prosthetic heart valve for replacing a native valve includes a collapsible and expandable stent having a proximal end, a distal end, and a plurality of struts defining a plurality of cells, the plurality of cells forming an aortic section, an annulus section and a subannular section of the stent, and a valve assembly disposed within the annulus section of the stent, the valve assembly including a plurality of leaflets. The struts of the annulus section may have a first average thickness and the struts of the subannular section have a second average thickness different from the first average thickness.

In some examples, the second average thickness may be less than the first average thickness. The second average thickness may be between about ⅓ to about ½ of the first average thickness.

In some embodiments, a prosthetic heart valve for replacing a native valve includes a collapsible and expandable stent extending in a length direction between a proximal end and a distal end, the stent including a plurality of struts defining a plurality of cells, the plurality of cells forming an aortic section, an annulus section and a subannular section of the stent, and a valve assembly disposed, within the annulus section of the stent, the valve assembly including a plurality of leaflets. The subannular section in an expanded condition of the stent may have a larger diameter than the annulus section in the expanded condition of the stent.

In some examples, the subannular section in the expanded condition of the stent may have a diameter between about 2 mm and about 6 mm larger than a diameter of the annulus section in the expanded condition of the stent. Each of the plurality of cells may have a length in the length direction and a width in a circumferential direction of the stent, and for each of the plurality of cells of the subannular section the length is less than the width in the expanded condition. Each of the plurality of cells may have a length in the length direction and a width in a circumferential direction of the stent, and for each of the plurality of cells of the subannular section the length is between about 5 mm and about 12 mm and the width is between about 9 mm and about 16 mm in the expanded condition.

In some embodiments, a method implanting a prosthetic heart valve includes delivering the prosthetic heart valve in a collapsed condition to the native valve annulus, the heart valve including: (i) a collapsible and expandable stent extending in a length direction between a proximal end. and a distal end and including a plurality of struts defining a plurality of cells, the plurality of cells forming an aortic section, an annulus section and a subannular section of the stent, each of the cells having a length in the length direction and a width in a circumferential direction of the stent, and (ii) a valve assembly disposed within the annulus section of the stent, the valve assembly including a plurality of leaflets; and transitioning the stent from the collapsed condition to an expanded condition, whereby the plurality of cells of the subannular section foreshorten in the length direction by a first relative amount and the plurality of cells of the annulus section foreshorten in the length direction by a second relative amount less than the first relative amount.

In some examples, the plurality of cells of the subannular section may foreshorten by between about 50% and about 100% and the plurality or cells or the annulus section foreshorten by between about 10% and about 18%. The plurality of cells of the subannular section may foreshorten between about three times and about five times more than the plurality of cells of the annulus section. When the stent transitions from the collapsed condition to the expanded condition, the plurality of cells of the subannular section may increase in width by between about 500% and about 1500% and the plurality of cells of the annulus section increase in width by between about 300% and about 1000%. When the stent transitions from the collapsed condition to the expanded condition, the plurality of cells of the subannular section may increase in width between about 1.6 times and about 1.1 times more than the plurality of cells of the annulus section.

It will be appreciated, that the various dependent claims and the features set forth therein can be combined in different ways than presented in the initial claims. It will also be appreciated that the features described in connection with individual embodiments may be snared with others of the described embodiments.

The invention claimed is:

1. A prosthetic heart valve for replacing a native valve, comprising:
    a collapsible and expandable stent extending in a length direction between a proximal end and a distal end, the stent including a plurality of struts defining a plurality of cells, the plurality of cells forming an aortic section, an annulus section and a subannular section of the stent, each of the cells having a length in the length direction and a width in a circumferential direction of the stent, the annulus section having a first diameter in an expanded condition of the stent, the aortic section having a second diameter in the expanded condition of the stent larger than the first diameter, each of the plurality of cells in the aortic section being larger than each of the plurality of cells in the annulus section; and
    a valve assembly directly coupled to the annulus section of the stent, the valve assembly including a plurality of leaflets;
    wherein, in the expanded condition of the stent, each of the plurality of cells of the subannular section has a width greater than its length, and each of the plurality of cells of the annulus section has a length greater than its width,
    wherein the struts of the subannular section have an average thickness less than an average thickness of the struts of the annulus section.

2. The prosthetic heart valve of claim 1, wherein the plurality of cells include a plurality of mitre-shaped transition cells disposed between the annulus section and the subannular section.

3. The prosthetic heart valve of claim 1, wherein the plurality of cells of the subannular section in the expanded condition are generally oval-shaped with upper and lower peaks.

4. The prosthetic heart valve of claim 1, wherein the average thickness of the struts of the subannular section between about ⅓ to about ½ of the average thickness of struts of the annulus section.

5. The prosthetic heart valve of claim 1, wherein the subannular section is configured and arranged to be disposed below leaflets of the native valve when the prosthetic valve replaces the native valve.

6. A prosthetic heart valve for replacing a native valve, comprising:
    a collapsible and expandable stent having a proximal end, a distal end, and a plurality of struts defining a plurality of cells, the plurality of cells forming an aortic section, an annulus section and a subannular section of the stent, the annulus section having a first diameter in an expanded condition of the stent, the aortic section having a second diameter in the expanded condition of the stent larger than the first diameter, each of the plurality of cells in the aortic section being larger than each of the plurality of cells in the annulus section; and
    a valve assembly disposed within the annulus section of the stent, the valve assembly including a plurality of leaflets,
    wherein the struts of the annulus section have a first average thickness and the struts of the subannular section have a second average thickness different from the first average thickness,
    wherein the second average thickness is between about ⅓ to about ½ of the first average thickness.

7. A prosthetic heart valve for replacing a native valve, comprising:
    a collapsible and expandable stent extending in a length direction between a proximal end and a distal end, the stent including a plurality of struts defining a plurality of cells, the plurality of cells forming an aortic section, an annulus section and a subannular section of the stent; and
    a valve assembly disposed within the annulus section of the stent, the valve assembly including a plurality of leaflets,
    wherein the subannular section in an expanded condition of the stent has a larger diameter than the annulus section in the expanded condition of the stent,
    wherein each of the plurality of cells has a length in the length direction and a width in a circumferential direction of the stent, and for each of the plurality of cells of the subannular section the length is between about 5 mm and about 12 mm and the width is between about 9 mm and about 16 mm in the expanded condition.

8. The prosthetic heart valve of claim 7, wherein the subannular section in the expanded condition of the stent has a diameter between about 2 mm and about 6 mm larger than a diameter of the annulus section in the expanded condition of the stent.

9. The prosthetic heart valve of claim 7, wherein for each of the plurality of cells of the subannular section the length is less than the width in the expanded condition.

* * * * *